US007005422B2

(12) United States Patent
Arora et al.

(10) Patent No.: US 7,005,422 B2
(45) Date of Patent: Feb. 28, 2006

(54) DERIVATIVES OF MONOSACCHARIDES AS CELL ADHESION INHIBITORS

(75) Inventors: Sudershan K Arora, Gurgaon (IN); Jang Bahadur Gupta, Gurgaon (IN); Vishwas D Joshi, New Delhi (IN)

(73) Assignee: Ranbaxy Laboratories Limited, New Delhi (IN)

(*) Notice: Subject to any disclaimer, the term of this patent is extended or adjusted under 35 U.S.C. 154(b) by 0 days.

(21) Appl. No.: 10/611,093

(22) Filed: Jul. 1, 2003

(65) Prior Publication Data

US 2004/0023900 A1 Feb. 5, 2004

Related U.S. Application Data

(62) Division of application No. 09/276,368, filed on Mar. 25, 1999, now Pat. No. 6,590,085.

(30) Foreign Application Priority Data

Jan. 15, 1999 (IN) ................................ 86/DEL/99

(51) Int. Cl.
*A61K 31/7052* (2006.01)
*A61K 31/7024* (2006.01)
*C07H 5/06* (2006.01)

(52) U.S. Cl. ............................ 514/42; 514/23; 514/25; 536/124; 536/18.7; 536/4.1; 536/17.2; 536/53; 536/123.1; 536/120; 536/116

(58) Field of Classification Search .................. 514/42, 514/25, 23; 536/126, 18.7, 4.1, 17.2, 53, 536/123, 123.1, 120, 116
See application file for complete search history.

(56) References Cited

U.S. PATENT DOCUMENTS

| 2,715,121 | A |   | 8/1955  | Glen et al.           |
|-----------|---|---|---------|-----------------------|
| 4,056,322 | A |   | 11/1977 | Gordon et al. ..... 536/4 |
| 4,735,934 | A |   | 4/1988  | Gordon ............ 514/25 |
| 4,996,195 | A |   | 2/1991  | Ronsen et al. ..... 514/23 |
| 5,010,058 | A |   | 4/1991  | Ronsen et al. ..... 514/23 |
| 5,637,570 | A | * | 6/1997  | Arora et al. ....... 514/25 |
| 6,590,085 | B1| * | 7/2003  | Arora et al. ...... 536/17.2 |

FOREIGN PATENT DOCUMENTS

| EP | 379397     | 7/1990  |
| EP | 404136     | 12/1990 |
| HU | 219453     | 8/1995  |
| WO | WO 91/04862| 4/1991  |
| WO | WO 92/00995| 1/1992  |
| WO | WO 94/11381| 5/1994  |

OTHER PUBLICATIONS

Bouveng, "Phenylisocyanate derivatives of carbohydrates.", Acta. Chem. Scand. 1961, 15, pp. 96-100.*

Abraham et al, "a$_4$ Integrins Mediate Antigen-induced Late Bronchial Responses and Prolonged Airway Hyper-responsiveness in Sheep,"*J. Clin. Invest.*, 93:776 (1994).
Aspinall et al, "The hex-5-enose degradation: zinc dust cleavage of 6-deoxy-6-iodo-a-D-galactopyranosicid linkages in methylated di- and trisaccharides," *Can. J. Chem.*, 62:2728-2735 (1984).
Baron et al, "Surface Expression of a4 Integrin by CD4 T Cells is Required for Their Entry into Brain Parenchyma," *J. Exp. Med.*, 177:57 (1993).
Bhattacharjee and Gorin, "Hydrogenolysis of carbohydrate acetals, ketals, and cyclic orthoesters with lithium aluminium hydride-aluminium trichloride," *Can. J. Chem.*, 47:1195 (1969).
Binkley, "Synthesis of Methyl 2,6-Dideoxy-3-C-Mathyl-a-D-Ribo-Hexopyranoside (Methyl a-D-Mycaroside), A Component of the Antitumor Agent Mithramycin," *J. Carbohydr. Chem.*, 4:227 (1985).
Bouveng, "Phenylisocyanate Derivatives of Carbohydrates," *Acta. Chem. Scand.*, 15:96-100 (1961).
Chisolm et al, "Monoclonal antibodes to the integgrin a-4 subunit inhibit the murine contact hypersensitivity response, " *Eur. J. Immunol.*, 23:682 (1993).
Ferguson et al, "Two integgrin-binding peptides abrogate T cell-mediated immune responses in vivo," *Proc. Natl. Acad. Sci (USA)*, 88:8072 (1991).
Hasegawa et al, Synthesis of N-[2-S-(2-Acetamido-2,3-Dideoxy-D-Glucopyranose-3-yl)-2-Thio-D-Lactoyl]-L-Alanyl-D-Isoglutamine, *J. Carbohydr. Chem.*, 3:331-341 (1984).
King and Allbutt, "Stereochemistry of bimolecular nucleophilic opening of a dioxolenium ring fused to an anchored cyclohexane system, "*Can. J. Chem.*, 47:1455 (1969).
King and Allbutt, "Remarkable Stereoselectivity in the hydrolysis of dioxolenium ions and orthoesters fused to anchored six-membered rings, "*Can. J. Chem.*, 48:1754 (1970).
Komoriya et al, "The Minimal Essence Sequence for a Major Cell Type-specific Adhesion Site (CS1) within the Alternatively Spliced Type III Connecting Segment Domain of Fibronectin Is Leucine-Aspartic Acid-Valine," *J. Biol. Chem.*, 266:15075 (1991).

(Continued)

*Primary Examiner*—James O. Wilson
*Assistant Examiner*—Devesh Khare
(74) *Attorney, Agent, or Firm*—Jayadeep R. Deshmukh, Esq.; George E. Heibel, Esq.

(57) ABSTRACT

This invention relates generally to compounds and processes for synthesizing derivatives of 2-3-O-isopropylidene-α-L-xylo-2-hexulofuranosonic acid. The compounds of this invention are useful, inter-alia, for the inhibition and prevention of cell adhesion and cell adhesion-mediated pathologies, including inflammatory and autoimmune diseases, such as bronchial asthma, rheumatoid arthritis, type I diabetes, multiple sclerosis, allograft rejection and psoriasis. This invention also relates to pharmacological compositions containing derivatives of 2-3-O-isopropylidene-α-L-xylo-2-hexulofuranosonic acid and the methods of treating such pathologies as listed above.

5 Claims, No Drawings

OTHER PUBLICATIONS

Mani et al, "Heparan/Chondroitin/Dermatan Sulfate Primer 2-(6-Hydroxynaphthyl)-O-β-D-Xylopyranoside Preferentially Inhibits Growth of Transformed Cells," *Cancer Res.*, 58, pp. 1099-1104 (1998).

"Monosaccharides," *Methods in Carbohydr. Chem.*, 1:107 (1962) & 1:191 (1962).

Nowlin et al, "A Novel Cyclic Pentapeptide Inhibits a4β1 and a 5 β 1 Integrin-mediated Cell Adhesion," *J. Biol. Chem.*, 268(27):20352 (1993).

Podolsky et al, "Attenuation of Colitis in the Cotton-top Tamarin by Anti-a4 integrin Monoclonan Antibody," *J. Clin. Invest.*, 92: 372 (1993).

Wahl et al, "Synthetic Fibronectin Peptides Suppress Arthritis in Rats by Interrupting Leukocyte Adhesion and Recruitment," *J. Clin. Invest.*, 94:655 (1994).

Yang et al, "Inhibition of insulitis and prevention of diabetes in nonobese diabetic mice by blocking L-selectin and very late anitgen 4 adhesion receptors," *Proc. Natl. Acad. Sci. (USA)*, 90:10494 (1993).

Yednock et al, "Prevention of experimental autoimmune encephalomyelitis by antibodies against a4β1 integrin," *Nature (Lond)*, 356:63 (1992).

\* cited by examiner

DERIVATIVES OF MONOSACCHARIDES AS CELL ADHESION INHIBITORS

This application is a divisional of U.S. patent application Ser. No. 09/276,368, filed Mar. 25, 1999, now issued as U.S. Pat. No. 6,590,085 on Jul. 8, 2003.

FIELD OF THE INVENTION

This invention relates generally to compounds and processes for synthesizing derivatives of 2-3-O-isopropylidene-α-L-xylo-2-hexulofuranosonic acid. The compounds of this invention are useful, inter-alia, for the inhibition and prevention of cell adhesion and cell adhesion-mediated pathologies, including inflammatory and autoimmune diseases, such as bronchial asthma, rheumatoid arthritis, type I diabetes, multiple sclerosis, allograft rejection and psoriasis. This invention also relates to pharmacological compositions containing derivatives of 2-3-O-isopropylidene-α-L-xylo-2-hexulofuranosonic acid and the methods of treating such pathologies as listed above.

BACKGROUND OF THE INVENTION

Cell adhesion is a process by which cells associate with each other and migrate towards a specific target localized within the extracellular matrix. Specialized molecules, called cell adhesion molecules (CAMs), mediate these reactions. CAMs have been demonstrated to participate in various cell-cell, cell-extracellular matrix, and platelet-platelet interactions. CAMs influence the leukocytes' adhesion to the vascular endothelium, their transendothelial migration, retention at extravascular sites, and activation of T cells and eosinophils. These processes are central to the pathogenesis of inflammatory and autoimmune diseases. Therefore, CAMs are considered potential targets for treating such disorders.

CAMs can be classified into three groups: integrins, selectins, and the immunoglobulin superfamily. Of these, integrins are the key mediators in the adhesive interactions between hemopoietic cells and their microenvironment. They are comprised of alpha-beta heterodimers and integrate signals from the outside to the inside of cells, and vice versa. Integrins can be classified on the basis of the beta subunits they contain. For example, the beta-1 subfamily contains beta-1 subunit noncovalently linked to one of the 10 different alpha subunits.

The alpha-4 beta-1 integrin, also known as $VLA_4$ (very late activation antigen 4), is a member of the beta-1 integrin family and comprises alpha-4 and beta-1 subunits. $VLA_4$ interacts with two specific ligands—the vascular cell adhesion molecule (VCAM-1) and the CS1 region of the protein fibronectin. Adhesion mediated by $VLA_4$ is central to the process of transendothelial migration of leukocytes. Ligation of $VLA_4$ is followed by gross rearrangement of the cytoskeleton, leading to flattening of cells along the blood vessel wall, followed by expression of specific molecules that digest the endothelial cell wall and diapedesis. Once in the extraluminal region, the interactions of $VLA_4$ with extracellular fibronectin play a crucial role in the migration of leukocytes to the site of inflammation, T cell proliferation, expression of cytokines and inflammatory mediators. Additionally, $VLA_4$ ligation provides co-stimulatory signals to the leukocytes, resulting in enhanced immunoreactivity. Thus, appropriate $VLA_4$ antagonists would, in theory, ameliorate the immune response through a twofold action—inhibition of T cell recruitment at the site of inflammation and inhibition of co-stimulatory activation of immune cells.

In this respect, inhibitors of $VLA_4$ interactions have been demonstrated to exhibit beneficial therapeutic effects in several animal models of inflammatory and allergic diseases, including sheep allergic asthma (Abraham et al, J. Clin. Invest. 1994;93:776); arthritis (Wahl et al, J. Clin. Invest. 1994;94:655); experimental allergic encephalomyelitis (Yednock et al, Nature (Lond), 1992;356:63 and Baron et al, J. Exp. Med. 1993;177:57); contact hypersensitivity (Chisolm et al, Eur J. Immunol. 1993;23:682); type I diabetes (Yang et al, Proc. Natl. Acad. Sci. (USA) 1993;90:10494); and inflammatory bowel disease (Podolsky et al, J. Clin. Invest. 1993;92:372).

The CS1 moiety region of fibronectin involved in the interaction with $VLA_4$ was identified as the tripeptide Leu-Asp-Val (LDV) (Komoriya et al, J. Biol. Chem. 1991;266:15075). Several peptides containing the LDV sequence were synthesized and shown to inhibit the in vivo interaction of $VLA_4$ to its ligands (Ferguson et al, Proc. Natl. Acad. Sci. (USA) 1991;88:8072; Wahl et al, J. Clin. Invest. 1994;94:655; Nowlin et al, J. Biol. Chem. 1993;268(27):20352; and PCT publication, WO91/4862).

Despite these advances a need for small and specific inhibitors of $VLA_4$-dependent cell adhesion molecules remains. Ideally, such inhibitors are water soluble with oral efficacy. Such compounds would provide useful agents for the treatment, prevention or suppression of various inflammatory pathologies mediated by $VLA_4$ binding.

It is generally known that isopropylidene and benzylidene groups are the most commonly used protective groups in carbohydrate chemistry. Although both groups are introduced into a molecule under similar conditions, the location of the protection can be quite different, and this difference is directly related to the stability of each protected molecule. Since protection normally occurs under conditions that allow reversibility, the reaction proceeds until equilibrium is reached. The distribution of products at equilibrium is determined by their relative thermodynamic stabilities. In other words, these reactions are thermodynamically controlled. Benzylidene groups prefer to be part of 6-membered ring acetals, while the ketals resulting from acetonation generally are 5-membered rings. The difference is attributed to the effect of the methyl and phenyl substituents on the stability of the particular ring systems. These blocking methods are described in the U.S. Pat. Nos. 2,715,121, 4,056,322, 4,735,934, 4,996,195 and 5,010,058, the disclosures of which are incorporated herein by reference. Other blocking methods are also described in J. Carbohydr. Chem. 1985;4:227 and 1984;3:331; Methods in Carbohydr. Chem. 1962;1:107 and 1962;1:191; Can J. Chem. 1984;62:2728, 1969;47:1195, 1455, and 1970;48:1754, all incorporated herein by reference. The prior art reveals that D-glucose is blocked at the 1,2;5,6-positions with either the isopropylidene or cyclohexylidene blocking group, leaving the 3-position open to undergo derivatization. The therapeutic activity of hexoses and their derivatives are also disclosed in some of the above-cited prior art.

The compounds of the present invention were screened for inhibitory activity in $VLA_4$-mediated cell adhesion assay and the classical murine hypersensitivity assay in mice. Several compounds exhibited significant inhibitory activity in both tests. The salts of these compounds could be easily solubilized in water and used in the treatment of chronic, cell adhesion-mediated, allergic, autoimmune and inflammatory disorders, such as bronchial asthma and rheumatoid arthritis.

Some of the prior art describes development of peptide derivatives as cell adhesion antagonists for treatment of these diseases. However, because treatment of chronic diseases requires. prolonged (mid-term to long-term) administration of drugs, the development of specific, orally available cell adhesion inhibitors would be very beneficial.

There is no example available in the prior art wherein the compounds, containing a sugar nucleus coupled with carbamate moiety, of the present invention are used as therapy for the inhibition, prevention and suppression of $VLA_4$-mediated cell adhesion and pathologies associated with that adhesion.

SUMMARY OF THE INVENTION

An object of the present invention is to provide a process for synthesizing a new class of compounds that exhibit significant activity as $VLA_4$ antagonists.

Most of the compounds described in U.S. Pat. No. 5,637, 570 have shown significant anti-cancer activities and were devoid of any anti-cell adhesion activities. Therefore, the compounds of the present invention were designed and synthesized so as to enhance their anti-cell adhesion properties. It was discovered that, for a compound to be active as a cell adhesion inhibitor, it is best if the sugar has a carbamate moiety along with other functionalities.

It is a further object of this invention to provide a process for the preparation of novel carbohydrate-based water-soluble compounds that exhibit significant activity to be used as cell adhesion antagonists.

Other objects and advantages of the present invention will be set forth in the description that follows, will be in part apparent from the description, or may be learned by the practice of the invention. The objects and advantages of this invention may be realized and obtained by means of the mechanisms and combinations pointed out in the appended claims.

In order to achieve the above-mentioned objects and in accordance with one aspect of the present invention, there is provided a process for the synthesis of monosaccharide derivatives and the derivatives themselves, having the structure of Formula I:

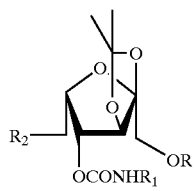

FORMULA I wherein R is $C_1$ to $C_{15}$ alkyl, alkene, alkyne (straight chain or branched), aryl, substituted aryl or alkylaryl, $R_1$ is phenyl, o,-m- or p-chlorophenyl, tolyl, methoxyphenyl or nitrophenyl and $R_2$ is H, pyrrolidinyl, piperidinyl, morphilinyl or hexamethyleneimino or a radical of the formula —$NHR_3$ wherein $R_3$ is $C_1$ to $C_{15}$ alkyl, alkene or alkyne (straight chain or branched) or a radical of Formula III.

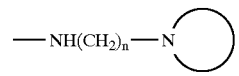

FORMULA III wherein n is a whole number up to 5 and

is a five-, six- or seven-membered heterocyclic ring containing one or more heteroatoms, and wherein preferably

is pyrrolidinyl, piperidinyl, morpholinyl or hexamethyleneimino moieties.

Preferred compounds are those wherein $R_1$ and $R_2$ are not H at the same time. Acid addition salts of the above compounds are also included in the invention.

In accordance with another aspect of the present invention there is provided a list of compounds as shown below in the description of the invention section.

In accordance with another aspect of the present invention there are provided methods of preventing, inhibiting or suppressing cell adhesion in an animal (the term animal as used herein includes humans or mammals), comprising administering to said animal, the compounds described above.

In accordance with another aspect of the present invention there is provided a method for treating an animal suffering from bronchial asthma, rheumatoid arthritis, multiple sclerosis, type I diabetes, psoriasis, allograft rejection, and other inflammatory and/or autoimmune disorders, comprising administering to said animal, the compounds described above.

In accordance with yet another aspect of the present invention there is provided a method for preventing, inhibiting or suppressing cell adhesion-associated inflammation with compounds described above.

In accordance with a further aspect of the present invention there is provided a method for preventing, inhibiting or suppressing a cell adhesion-associated immune or autoimmune response with the compounds described above.

In accordance with another aspect of the present invention there is provided a method for treating or preventing a disease selected from the group consisting of asthma, arthritis, psoriasis, allograft rejection, multiple sclerosis, diabetes and inflammatory bowel disease, with the compounds as described above.

The compounds of the present invention are novel and exhibit significant potency in terms of their activity, which was determined by in vitro $VLA_4$-mediated cell adhesion assay and in vivo mouse ear swelling test. The compounds that were found active in in vitro assay were tested in vivo. Some of the compounds of the present invention were found to be potent $VLA_4$ antagonists. Therefore, the present invention provides the pharmaceutical compositions for the possible treatment of bronchial asthma and other inflammatory and autoimmune disorders. In addition, the compounds of the above invention can be administered orally or parenterally.

DETAILED DESCRIPTION OF THE INVENTION

The compounds of the present invention may be prepared by techniques well-known in the art and familiar to the average synthetic organic chemist. In addition, the compounds of the present invention may be prepared by the following novel and inventive reaction sequence, which also show preferred R, $R_1$ and $R_2$ groups.

SCHEME I

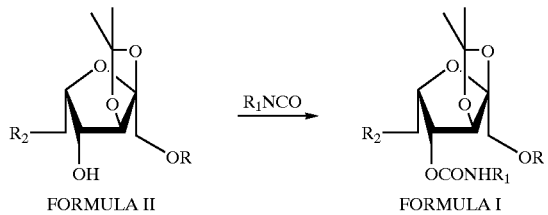

2,3-O-Isopropyl-1-0-alkyl or arylalkyl-6-deoxy-6-amino-substituted-L-xylo-2-hexulofuranose compounds of Formula II, as shown in Scheme I, are prepared according to the method described in U.S. Pat. No. 5,637,570 and are the intermediates for the synthesis of the compounds of Formula I of the present invention. Thus, the following intermediates were prepared following the process as described in U.S. Pat. No. 5,637,570:

2,3-O-isopropylidene-6-deoxy-6-hexamethyleneimino-1-O-dodecyl-α-L-xylo-2-hexulofuranose
2,3-O-isopropylidene-6-deoxy-6-hexamethyleneimino-1-O-decyl-α-L-xylo-2-hexulofuranose
2,3-O-isopropylidene-6-deoxy-6-hexamethyleneimino-1-O-heptyl-α-L-xylo-2-hexulofuranose
2,3-O-isopropylidene-6-deoxy-6-pyrrolidinyl-1-O-dodecyl-α-L-xylo-2-hexulofuranose
2,3-O-isopropylidene-6-deoxy-6-pyrrolidinyl-1-O-decyl-α-L-xylo-2-hexulofuranose
2,3-O-isopropylidene-6-deoxy-6-pyrrolidinyl-1-O-heptyl-α-L-xylo-2-hexulofuranose
2,3-O-isopropylidene-6-deoxy-6-morphilinyl-1-O-dodecyl-α-L-xylo-2-hexulofuranose
2,3-O-isopropylidene-6-deoxy-6-morphilinyl-1-O-decyl-α-L-xylo-2-hexulofuranose
2,3-O-isopropylidene-6-deoxy-6-morphilinyl-1-O-heptyl-α-L-xylo-2-hexulofuranose
2,3-O-isopropylidene-6-deoxy-6-piperidinyl-1-O-dodecyl-α-L-xylo-2-hexulofuranose
2,3-O-isopropylidene-6-deoxy-6-piperidinyl-1-O-decyl-α-L-xylo-2-hexulofuranose
2,3-O-isopropylidene-6-deoxy-6-piperidinyl-1-O-heptyl-α-L-xylo-2-hexulofuranose
2,3-O-isopropylidene-6-deoxy-6-ethylpyrrolidinyl-1-O-dodecyl-α-L-xylo-2-hexulofuranose
2,3-O-isopropylidene-6-deoxy-6-ethylpyrrolidinyl-1-O-decyl-α-L-xylo-2-hexulofuranose
2,3-O-isopropylidene-6-deoxy-6-ethylpyrrolidinyl-1-O-heptyl-α-L-xylo-2-hexulofuranose
2,3-O-isopropylidene-6-deoxy-6-ethylmorpholinyl-1-O-dodecyl-α-L-xylo-2-hexulofuranose
2,3-O-isopropylidene-6-deoxy-6-ethylmorpholinyl-1-O-decyl-α-L-xylo-2-hexulofuranose
2,3-O-isopropylidene-6-deoxy-6-ethylmorpholinyl-1-O-heptyl-α-L-xylo-2-hexulofuranose.

Thus, the compound of Formula II is treated with an appropriate isocyanate in a suitable solvent at low temperature, preferably at 0–10° C. to afford the compounds of Formula I of the present invention. An illustrative list of particular compounds according to the invention and capable of being produced by Scheme I include:

| Compound No. | Chemical Name |
|---|---|
| 01. | 2,3-O-Isopropylidene-1-O-decyl-4-(methylcarbamate)-6-deoxy-6-pyrrolidinyl-α-L-xylo-2-hexulofuranose |
| 02. | 2,3-O-Isopropylidene-1-O-dodecyl-4-(methylcarbamate)-6-deoxy-6-pyrrolidinyl-α-L-xylo-2-hexulofuranose |
| 03. | 2,3-O-Isopropylidene-1-O-dodecyl-4-(phenylcarbamate)-6-deoxy-6-pyrrolidinyl-α-L-xylo-2-hexulofuranose |
| 04. | 2,3-O-Isopropylidene-1-O-dodecyl-4-(p-chlorophenylcarbamate)-6-deoxy-6-pyrrolidinyl-α-L-xylo-2-hexulofuranose |
| 05. | 2,3-O-Isopropylidene-1-O-dodecyl-4-(p-tolylcarbamate)-6-deoxy-6-pyrrolidinyl-α-L-xylo-2-hexulofuranose |
| 06. | 2,3-O-Isopropylidene-1-O-dodecyl-4-(p-methoxyphenylcarbamate)-6-deoxy-6-pyrrolidinyl-α-L-xylo-2-hexulofuranose |
| 07. | 2,3-O-Isopropylidene-1-O-dodecyl-4-(p-nitrophenylcarbamate)-6-deoxy-6-pyrrolidinyl-α-L-xylo-2-hexulofuranose |
| 08. | 2,3-O-Isopropylidene-1-O-decyl-4-(phenylcarbamate)-6-deoxy-6-pyrrolidinyl-α-L-xylo-2-hexulofuranose |
| 09. | 2,3-O-Isopropylidene-1-O-decyl-4-(p-chlorophenylcarbamate)-6-deoxy-6-pyrrolidinyl-α-L-xylo-2-hexulofuranose |
| 10. | 2,3-O-Isopropylidene-1-O-decyl-4-(p-tolylcarbamate)-6-deoxy-6-pyrrolidinyl-α-L-xylo-2-hexulofuranose |
| 11. | 2,3-O-Isopropylidene-1-O-decyl-4-(p-methoxyphenylcarbamate)-6-deoxy-6-pyrrolidinyl-α-L-xylo-2-hexulofuranose |
| 12. | 2,3-O-Isopropylidene-1-O-decyl-4-(p-nitrophenylcarbamate)-6-deoxy-6-pyrrolidinyl-α-L-xylo-2-hexulofuranose |
| 13. | 2,3-O-Isopropylidene-1-O-heptyl-4-(phenylcarbamate)-6-deoxy-6-pyrrolidinyl-α-L-xylo-2-hexulofuranose |

-continued

| Compound No. | Chemical Name |
|---|---|
| 14. | 2,3-O-Isopropylidene-1-O-heptyl-4-(p-chlorophenylcarbamate)-6-deoxy-6-pyrrolidinyl-α-L-xylo-2-hexulofuranose |
| 15. | 2,3-O-Isopropylidene-1-O-heptyl-4-(p-tolylcarbamate)-6-deoxy-6-pyrrolidinyl-α-L-xylo-2-hexulofuranose |
| 16. | 2,3-O-Isopropylidene-1-O-heptyl-4-(p-methoxyphenylcarbamate)-6-deoxy-6-pyrrolidinyl-α-L-xylo-2-hexulofuranose |
| 17. | 2,3-O-Isopropylidene-1-O-heptyl-4-(p-nitrophenylcarbamate)-6-deoxy-6-pyrrolidinyl-α-L-xylo-2-hexulofuranose |
| 18. | 2,3-O-Isopropylidene-1-O-dodecyl-4-(phenylcarbamate)-6-deoxy-6-morpholinyl-α-L-xylo-2-hexulofuranose |
| 19. | 2,3-O-Isopropylidene-1-O-dodecyl-4-(p-chlorophenylcarbamate)-6-deoxy-6-morpholinyl-α-L-xylo-2-hexulofuranose |
| 20. | 2,3-O-Isopropylidene-1-O-dodecyl-4-(p-tolylcarbamate)-6-deoxy-6-morpholinyl-α-L-xylo-2-hexulofuranose |
| 21. | 2,3-O-Isopropylidene-1-O-dodecyl-4-(p-methoxyphenylcarbamate)-6-deoxy-6-morpholinyl-α-L-xylo-2-hexulofuranose |
| 22. | 2,3-O-Isopropylidene-1-O-dodecyl-4-(p-nitrophenylcarbamate)-6-deoxy-6-morpholinyl-α-L-xylo-2-hexulofuranose |
| 23. | 2,3-O-Isopropylidene-1-O-decyl-4-(phenylcarbamate)-6-deoxy-6-morpholinyl-α-L-xylo-2-hexulofuranose |
| 24. | 2,3-O-Isopropylidene-1-O-decyl-4-(p-chlorophenylcarbamate)-6-deoxy-6-morpholinyl-α-L-xylo-2-hexulofuranose |
| 25. | 2,3-O-Isopropylidene-1-O-decyl-4-(p-tolylcarbamate)-6-deoxy-6-morpholinyl-α-L-xylo-2-hexulofuranose |
| 26. | 2,3-O-Isopropylidene-1-O-decyl-4-(p-methoxyphenylcarbamate)-6-deoxy-6-morpholinyl-α-L-xylo-2-hexulofuranose |
| 27. | 2,3-O-Isopropylidene-1-O-decyl-4-(p-nitrophenylcarbamate)-6-deoxy-6-morpholinyl-α-L-xylo-2-hexulofuranose |
| 28. | 2,3-O-Isopropylidene-1-O-heptyl-4-(phenylcarbamate)-6-deoxy-6-morpholinyl-α-L-xylo-2-hexulofuranose |
| 29. | 2,3-O-Isopropylidene-1-O-heptyl-4-(p-chlorophenylcarbamate)-6-deoxy-6-morpholinyl-α-L-xylo-2-hexulofuranose |
| 30. | 2,3-O-Isopropylidene-1-O-heptyl-4-(p-tolylcarbamate)-6-deoxy-6-morpholinyl-α-L-xylo-2-hexulofuranose |
| 31. | 2,3-O-Isopropylidene-1-O-heptyl-4-(p-methoxyphenylcarbamate)-6-deoxy-6-morpholinyl-α-L-xylo-2-hexulofuranose |
| 32. | 2,3-O-Isopropylidene-1-O-heptyl-4-(p-nitrophenylcarbamate)-6-deoxy-6-morpholinyl-α-L-xylo-2-hexulofuranose |
| 33. | 2,3-O-Isopropylidene-1-O-dodecyl-4-(phenylcarbamate)-6-deoxy-6-piperidinyl-α-L-xylo-2-hexulofuranose |
| 34. | 2,3-O-Isopropylidene-1-O-dodecyl-4-(p-chlorophenylcarbamate)-6-deoxy-6-piperidinyl-α-L-xylo-2-hexulofuranose |
| 35. | 2,3-O-Isopropylidene-1-O-dodecyl-4-(p-tolylcarbamate)-6-deoxy-6-piperidinyl-α-L-xylo-2-hexulofuranose |
| 36. | 2,3-O-Isopropylidene-1-O-dodecyl-4-(p-methoxyphenylcarbamate)-6-deoxy-6-piperidinyl-α-L-axylo-2-hexulofuranose |
| 37. | 2,3-O-Isopropylidene-1-O-dodecyl-4-(p-nitrophenylcarbamate)-6-deoxy-6-piperidinyl-α-L-xylo-2-hexulofuranose |
| 38. | 2,3-O-Isopropylidene-1-O-decyl-4-(phenylcarbamate)-6-deoxy-6-piperidinyl-α-L-xylo-2-hexulofuranose |
| 39. | 2,3-O-Isopropylidene-1-O-decyl-4-(p-chlorophenylcarbamate)-6-deoxy-6-piperidinyl-α-L-xylo-2-hexulofuranose |
| 40. | 2,3-O-Isopropylidene-1-O-decyl-4-(p-tolylcarbamate)-6-deoxy-6-piperidinyl-α-L-xylo-2-hexulofuranose |
| 41. | 2,3-O-Isopropylidene-1-O-decyl-4-(p-methoxyphenylcarbamate)-6-deoxy-6-piperidinyl-α-L-xylo-2-hexulofuranose |
| 42. | 2,3-O-Isopropylidene-1-O-decyl-4-(p-nitrophenylcarbamate)-6-deoxy-6-piperidinyl-α-L-xylo-2-hexulofuranose |
| 43. | 2,3-O-Isopropylidene-1-O-heptyl-4-(phenylcarbamate)-6-deoxy-6-piperidinyl-α-L-xylo-2-hexulofuranose |
| 44. | 2,3-O-Isopropylidene-1-O-heptyl-4-(p-chlorophenylcarbamate)-6-deoxy-6-piperidinyl-α-L-xylo-2-hexulofuranose |
| 45. | 2,3-O-Isopropylidene-1-O-heptyl-4-(p-tolylcarbamate)-6-deoxy-6-piperidinyl-α-L-xylo-2-hexulofuranose |
| 46. | 2,3-O-Isopropylidene-1-O-heptyl-4-(p-methoxyphenylcarbamate)-6-deoxy-6-piperidinyl-α-L-xylo-2-hexulofuranose |
| 47. | 2,3-O-Isopropylidene-1-O-heptyl-4-(p-nitrophenylcarbamate)-6-deoxy-6-piperidinyl-α-L-xylo-2-hexulofuranose |
| 48. | 2,3-O-Isopropylidene-1-O-dodecyl-4-(phenylcarbamate)-6-deoxy-6-hexamethyleneimino-α-L-xylo-2-hexulofuranose |
| 49. | 2,3-O-Isopropylidene-1-O-dodecyl-4-(p-chlorophenylcarbamate)-6-deoxy-6-hexamethyleneimino-α-L-xylo-2-hexulofuranose |
| 50. | 2,3-O-Isopropylidene-1-O-dodecyl-4-(p-tolylcarbamate)-6-deoxy-6-hexamethyleneimino-α-L-xylo-2-hexulofuranose |
| 51. | 2,3-O-Isopropylidene-1-O-dodecyl-4-(p-methoxyphenylcarbamate)-6-deoxy-6-hexamethyleneimino-α-L-xylo-2-hexulofuranose |

-continued

| Compound No. | Chemical Name |
|---|---|
| 52. | 2,3-O-Isopropylidene-1-O-dodecyl-4-(p-nitrophenylcarbamate)-6-deoxy-6-hexamethyleneimino-α-L-xylo-2-hexulofuranose |
| 53. | 2,3-O-Isopropylidene-1-O-decyl-4-(phenylcarbamate)-6-deoxy-6-hexamethyleneimino-α-L-xylo-2-hexulofuranose |
| 54. | 2,3-O-Isopropylidene-1-O-decyl-4-(p-chlorophenylcarbamate)-6-deoxy-6-hexamethyleneimino-α-L-xylo-2-hexulofuranose |
| 55. | 2,3-O-Isopropylidene-1-O-decyl-4-(p-tolylcarbamate)-6-deoxy-6-hexamethyleneimino-α-L-xylo-2-hexulofuranose |
| 56. | 2,3-O-Isopropylidene-1-O-decyl-4-(p-methoxyphenylcarbamate)-6-deoxy-6-hexamethyleneimino-α-L-xylo-2-hexulofuranose |
| 57. | 2,3-O-Isopropylidene-1-O-decyl-4-(p-nitrophenylcarbamate)-6-deoxy-6-hexamethyleneimino-α-L-xylo-2-hexulofuranose |
| 58. | 2,3-O-Isopropylidene-1-O-heptyl-4-(phenylcarbamate)-6-deoxy-6-hexamethyleneimino-α-L-xylo-2-hexulofuranose |
| 59. | 2,3-O-Isopropylidene-1-O-heptyl-4-(p-chlorophenylcarbamate)-6-deoxy-6-hexamethyleneimino-α-L-xylo-2-hexulofuranose |
| 60. | 2,3-O-Isopropylidene-1-O-heptyl-4-(p-tolylcarbamate)-6-deoxy-6-hexamethyleneimino-α-L-xylo-2-hexulofuranose |
| 61. | 2,3-O-Isopropylidene-1-O-heptyl-4-(p-methoxyphenylcarbamate)-6-deoxy-6-hexamethyleneimino-α-L-xylo-2-hexulofuranose |
| 62. | 2,3-O-Isopropylidene-1-O-heptyl-4-(p-nitrophenylcarbamate)-6-deoxy-6-hexamethyleneimino-α-L-xylo-2-hexulofuranose |
| 63. | 2,3-O-Isopropylidene-1-O-dodecyl-4-(phenylcarbamate)-6-deoxy-6-(2-ethylpyrrolidinyl)-α-L-xylo-2-hexulofuranose |
| 64. | 2,3-O-Isopropylidene-1-O-dodecyl-4-(p-chlorophenylcarbamate)-6-deoxy-6-(2-ethylpyrrolidinyl)-α-L-xylo-2-hexulofuranose |
| 65. | 2,3-O-Isopropylidene-1-O-dodecyl-4-(p-tolylcarbamate)-6-deoxy-6-(2-ethylpyrrolidinyl)-α-L-xylo-2-hexulofuranose |
| 66. | 2,3-O-Isopropylidene-1-O-dodecyl-4-(p-methoxyphenylcarbamate)-6-deoxy-6-(2-ethylpyrrolidinyl)-α-L-xylo-2-hexulofuranose |
| 67. | 2,3-O-Isopropylidene-1-O-dodecyl-4-(p-nitrophenylcarbamate)-6-deoxy-6-(2-ethylpyrrolidinyl)-α-L-xylo-2-hexulofuranose |
| 68. | 2,3-O-Isopropylidene-1-O-decyl-4-(phenylcarbamate)-6-deoxy-6-(2-ethylpyrrolidinyl)-α-L-xylo-2-hexulofuranose |
| 69. | 2,3-O-Isopropylidene-1-O-decyl-4-(p-chlorophenylcarbamate)-6-deoxy-6-(2-ethylpyrrolidinyl)-α-L-xylo-2-hexulofuranose |
| 70. | 2,3-O-Isopropylidene-1-O-decyl-4-(p-tolylcarbamate)-6-deoxy-6-(2-ethylpyrrolidinyl)-α-L-xylo-2-hexulofuranose |
| 71. | 2,3-O-Isopropylidene-1-O-decyl-4-(p-methoxyphenylcarbamate)-6-deoxy-6-(2-ethylpyrrolidinyl)-α-L-xylo-2-hexulofuranose |
| 72. | 2,3-O-Isopropylidene-1-O-decyl-4-(p-nitrophenylcarbamate)-6-deoxy-6-(2-ethylpyrrolidinyl)-α-L-xylo-2-hexulofuranose |
| 73. | 2,3-O-Isopropylidene-1-O-heptyl-4-(phenylcarbamate)-6-deoxy-6-(2-ethylpyrrolidinyl)-α-L-xylo-2-hexulofuranose |
| 74. | 2,3-O-Isopropylidene-1-O-heptyl-4-(p-chlorophenylcarbamate)-6-deoxy-6-(2-ethylpyrrolidinyl)-α-L-xylo-2-hexulofuranose |
| 75. | 2,3-O-Isopropylidene-1-O-heptyl-4-(p-tolylcarbamate)-6-deoxy-6-(2-ethylpyrrolidinyl)-α-L-xylo-2-hexulofuranose |
| 76. | 2,3-O-Isopropylidene-1-O-heptyl-4-(p-methoxyphenylcarbamate)-6-deoxy-6-(2-ethylpyrrolidinyl)-α-L-xylo-2-hexulofuranose |
| 77. | 2,3-O-Isopropylidene-1-O-heptyl-4-(p-nitrophenylcarbamate)-6-deoxy-6-(2-ethylpyrrolidinyl)-α-L-xylo-2-hexulofuranose |
| 78. | 2,3-O-Isopropylidene-1-O-dodecyl-4-(phenylcarbamate)-6-deoxy-6-(2-ethylpiperidinyl)-α-L-xylo-2-hexulofuranose |
| 79. | 2,3-O-Isopropylidene-1-O-dodecyl-4-(p-chlorophenylcarbamate)-6-deoxy-6-(2-ethylpiperidinyl)-α-L-xylo-2-hexulofuranose |
| 80. | 2,3-O-Isopropylidene-1-O-dodecyl-4-(p-tolylcarbamate)-6-deoxy-6-(2-ethylpiperidinyl)-α-L-xylo-2-hexulofuranose |
| 81. | 2,3-O-Isopropylidene-1-O-dodecyl-4-(p-methoxyphenylcarbamate)-6-deoxy-6-(2-ethylpiperidinyl)-α-L-xylo-2-hexulofuranose |
| 82. | 2,3-O-Isopropylidene-1-O-dodecyl-4-(p-nitrophenylcarbamate)-6-deoxy-6-(2-ethylpiperidinyl)-α-L-xylo-2-hexulofuranose |
| 83. | 2,3-O-Isopropylidene-1-O-decyl-4-(phenylcarbamate)-6-deoxy-6-(2-ethylpiperidinyl)-α-L-xylo-2-hexulofuranose |
| 84. | 2,3-O-Isopropylidene-1-O-decyl-4-(p-chlorophenylcarbamate)-6-deoxy-6-(2-ethylpiperidinyl)-α-L-xylo-2-hexulofuranose |
| 85. | 2,3-O-Isopropylidene-1-O-decyl-4-(p-tolylcarbamate)-6-deoxy-6-(2-ethylpiperidinyl)-α-L-xylo-2-hexulofuranose |
| 86. | 2,3-O-Isopropylidene-1-O-decyl-4-(p-methoxyphenylcarbamate)-6-deoxy-6-(2-ethylpiperidinyl)-α-L-xylo-2-hexulofuranose |
| 87. | 2,3-O-Isopropylidene-1-O-decyl-4-(p-nitrophenylcarbamate)-6-deoxy-6-(2-ethylpiperidinyl)-α-L-xylo-2-hexulofuranose |
| 88. | 2,3-O-Isopropylidene-1-O-heptyl-4-(phenylcarbamate)-6-deoxy-6-(2-ethylpiperidinyl)-α-L-xylo-2-hexulofuranose |

-continued

| Compound No. | Chemical Name |
|---|---|
| 89. | 2,3-O-Isopropylidene-1-O-heptyl-4-(p-chlorophenylcarbamate)-6-deoxy-6-(2-ethylpiperidinyl)-α-L-xylo-2-hexulofuranose |
| 90. | 2,3-O-Isopropylidene-1-O-heptyl-4-(p-tolylcarbamate)-6-deoxy-6-(2-ethylpiperidinyl)-α-L-xylo-2-hexulofuranose |
| 91. | 2,3-O-Isopropylidene-1-O-heptyl-4-(p-methoxyphenylcarbamate)-6-deoxy-6-(2-ethylpiperidinyl)-α-L-xylo-2-hexulofuranose |
| 92. | 2,3-O-Isopropylidene-1-O-heptyl-4-(p-nitrophenylcarbamate)-6-deoxy-6-(2-ethylpiperidinyl)-α-L-xylo-2-hexulofuranose |
| 93. | 2,3-O-Isopropylidene-1-O-dodecyl-4-(phenylcarbamate)-6-deoxy-6-(2-ethylmorphilinyl)-α-L-xylo-2-hexulofuranose |
| 94. | 2,3-O-Isopropylidene-1-O-dodecyl-4-(p-chlorophenylcarbamate)-6-deoxy-6-(2-ethylmorphilinyl)-α-L-xylo-2-hexulofuranose |
| 95. | 2,3-O-Isopropylidene-1-O-dodecyl-4-(p-tolylcarbamate)-6-deoxy-6-(2-ethylmorphilinyl)-α-L-xylo-2-hexulofuranose |
| 96. | 2,3-O-Isopropylidene-1-O-dodecyl-4-(p-methoxyphenylcarbamate)-6-deoxy-6-(2-ethylmorphilinyl)-α-L-xylo-2-hexulofuranose |
| 97. | 2,3-O-Isopropylidene-1-O-dodecyl-4-(p-nitrophenylcarbamate)-6-deoxy-6-(2-ethylmorphilinyl)-α-L-xylo-2-hexulofuranose |
| 98. | 2,3-O-Isopropylidene-1-O-decyl-4-(phenylcarbamate)-6-deoxy-6-(2-ethylmorphilinyl)-α-L-xylo-2-hexulofuranose |
| 99. | 2,3-O-Isopropylidene-1-O-decyl-4-(p-chlorophenylcarbamate)-6-deoxy-6-(2-ethylmorphilinyl)-α-L-xylo-2-hexulofuranose |
| 100. | 2,3-O-Isopropylidene-1-O-decyl-4-(p-tolylcarbamate)-6-deoxy-6-(2-ethylmorphilinyl)-α-L-xylo-2-hexulofuranose |
| 101. | 2,3-O-Isopropylidene-1-O-decyl-4-(p-methoxyphenylcarbamate)-6-deoxy-6-(2-ethylmorphilinyl)-α-L-xylo-2-hexulofuranose |
| 102. | 2,3-O-Isopropylidene-1-O-dodecyl-4-(p-nitrophenylcarbamate)-6-deoxy-6-(2-ethylmorphilinyl)-α-L-xylo-2-hexulofuranose |
| 103. | 2,3-O-Isopropylidene-1-O-heptyl-4-(phenylcarbamate)-6-deoxy-6-(2-ethylmorphilinyl)-α-L-xylo-2-hexulofuranose |
| 104. | 2,3-O-Isopropylidene-1-O-heptyl-4-(p-chlorophenylcarbamate)-6-deoxy-6-(2-ethylmorphilinyl)-α-L-xylo-2-hexulofuranose |
| 105. | 2,3-O-Isopropylidene-1-O-heptyl-4-(p-tolylcarbamate)-6-deoxy-6-(2-ethylmorphilinyl)-α-L-xylo-2-hexulofuranose |
| 106. | 2,3-O-Isopropylidene-1-O-heptyl-4-(p-methoxyphenylcarbamate)-6-deoxy-6-(2-ethylmorphilinyl)-α-L-xylo-2-hexulofuranose |
| 107. | 2,3-O-Isopropylidene-1-O-heptyl-4-(p-nitrophenylcarbamate)-6-deoxy-6-(2-ethylmorphilinyl)-α-L-xylo-2-hexulofuranose |
| 108. | 2,3-O-Isopropylidene-1-O-dodecyl-4-(methylcarbamate)-6-deoxy-6-hexamethyleneimino-α-L-xylo-2-hexulofuranose |
| 109. | 2,3-O-Isopropylidene-1-O-dodecyl-4-(methylcarbamate)-6-deoxy-6-morpholinyl-α-L-xylo-2-hexulofuranose |
| 110. | 2,3-O-Isopropylidene-1-O-dodecyl-4-(methylcarbamate)-6-deoxy-6-piperidinyl-α-L-xylo-2-hexulofuranose |
| 111. | 2,3-O-Isopropylidene-1-O-dodecyl-4-(methylcarbamate)-6-deoxy-6-(2-ethylpyrroldinyl)-α-L-xylo-2-hexulofuranose |
| 112. | 2,3-O-Isopropylidene-1-O-dodecyl-4-(methylcarbamate)-6-deoxy-6-(2-ethylmorpholinyl)-α-L-xylo-2-hexulofuranose |
| 113. | 2,3-O-Isopropylidene-1-O-decyl-4-(methylcarbamate)-6-deoxy-6-morpholinyl-α-L-xylo-2-hexulofuranose |
| 114. | 2,3-O-Isopropylidene-1-O-decyl-4-(methylcarbamate)-6-deoxy-6-hexamethyleneimino-α-L-xylo-2-hexulofuranose |
| 115. | 2,3-O-Isopropylidene-1-O-decyl-4-(methylcarbamate)-6-deoxy-6-piperidinyl-α-L-xylo-2-hexulofuranose |
| 116. | 2,3-O-Isopropylidene-1-O-decyl-4-(methylcarbamate)-6-deoxy-6-(2-ethylpyrrolidinyl)-α-L-xylo-2-hexulofuranose |
| 117. | 2,3-O-Isopropylidene-1-O-decyl-4-(methylcarbamate)-6-deoxy-6-(2-ethylmorpholinyl)-α-L-xylo-2-hexulofuranose |
| 118. | 2,3-O-Isopropylidene-1-O-heptyl-4-(methylcarbamate)-6-deoxy-6-pyrrolidinyl-α-L-xylo-2-hexulofuranose |
| 119. | 2,3-O-Isopropylidene-1-O-heptyl-4-(methylcarbamate)-6-deoxy-6-morpholinyl-α-L-xylo-2-hexulofuranose |
| 120. | 2,3-O-Isopropylidene-1-O-heptyl-4-(methylcarbamate)-6-deoxy-6-hexamethyleneimino-α-L-xylo-2-hexulofuranose |
| 121. | 2,3-O-Isopropylidene-1-O-heptyl-4-(methylcarbamate)-6-deoxy-6-piperidinyl-α-L-xylo-2-hexulofuranose |
| 122. | 2,3-O-Isopropylidene-1-O-heptyl-4-(methylcarbamate)-6-deoxy-6-(2-ethylpyrrolidinyl)-α-L-xylo-2-hexulofuranose |
| 123. | 2,3-O-Isopropylidene-1-O-heptyl-4-(methylcarbamate)-6-deoxy-6-(2-ethylmorpholinyl)-α-L-xylo-2-hexulofuranose. |

The sugar derivatives of the present invention exhibit various pharmacological properties and are useful for treating animals; the term animal as defined herein includes human or mammal, with various inflammatory and autoimmune disorders, such as bronchial asthma, rheumatoid arthritis, type I diabetes, multiple sclerosis, allograft rejection and psoriasis.

The free amino compounds of the present invention: are basic and form organic and inorganic acid salts. The resulting salts, are useful by themselves and in the therapeutic composition and method of use. These salts may be prepared by the usual prior art techniques, such as suspending the compound in water and then adding one equivalent of the desired organic or mineral acid. Examples of preferred acids include hydrochloric, sulphuric, nitric, maleic, benzoic, tartaric, acetic, p-aminobenzoic, oxalic, succinic and glucoronic acid.

The neutral solution of the resulting salt is subjected to rotary evaporation under diminished pressure to the volume necessary to ensure precipitation of the salt upon cooling, which is then filtered and dried. The salts of the present invention may also be prepared strictly under non-aqueous conditions. For example, dissolving the free amine in a suitable organic solvent, adding exactly one equivalent of the desired acid to the same solvent and stirring the solution at 0–5° C. causes precipitation of the amine salt, which is then filtered, washed with solvent and dried. The amine salts are often preferred for use in formulating the therapeutic compositions as they are crystalline and relatively more stable and non-hydroscopic. The amine salts are also better adapted for intramuscular injection than are the free amines.

Because of their valuable pharmacological properties, the compounds of the present invention may be administered to an animal for treatment orally, topically, rectally, internasally or by parenteral route. When the therapeutic composition is to be administered orally, it is preferred that the compounds of the present invention are admixed with a filler and/or binder, such as starch and a disintegrator. The admixture may be pressed into a tablet conveniently sized for oral administration. Capsules may also be filled with the powdered therapeutic composition for oral administration. Alternatively, a water solution of the amine salt or suspension of the therapeutic composition may be admixed with a flavored syrup and administered orally. A salt of the free acid is usually preferred when the compound is administered by parenteral route.

The pharmaceutical compositions of the present invention are preferably produced and administered in dosage units, with each unit containing a certain amount of at least one compound of the invention and/or at least one physiologically acceptable base salt addition thereof. The dosage may be varied over extremely wide limits, as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formula I. In general, such prodrugs will be functional. derivatives of these compounds which are readily converted in vivo into the defined compounds. Conventional procedures for the selection and preparation of suitable prodrugs are known.

The present invention also includes the enantiomers, diastereomers, N-oxides, polymorphs and pharmaceutically acceptable salts of these compounds as well as metabolites having the same type of activity. This invention further includes pharmaceutical compositions comprising the molecules of Formula I or prodrugs, metabolite enantiomers, diastereomers, N-oxides, polymorphs or pharmaceutically acceptable salts thereof, in combination with pharmaceutically acceptable carriers and optionally included excipients.

The examples mentioned below demonstrate the general synthetic procedure as well as the specific preparation of the preferred compounds. The examples are provided to illustrate the details of the invention and should not be considered to limit the scope of the present invention.

EXPERIMENTAL DETAILS

Various solvents, such as acetone, methanol, pyridine, ether, tetrahydrofuran, hexane and dichloromethane, were dried using various drying agents according to the procedure described in the literature. Wet solvents gave poor yields of the products and intermediates. IR spectra were recorded as nujol mulls or a thin neat film on a Perkin Elmer Paragon instrument. Nuclear Magnetic Resonance (NMR) data (H, C) were recorded using a Varian XL-300 MHz instrument using tetramethylsilane as an internal standard. Chemical Ionization Mass Spectra (CIMS) were obtained using a Finnigan MAT-4510 mass spectrometer equipped with an INCOS data system. Generally, a direct exposure probe and methane as the reagent gas (0.33 mmHg, 120° C. source temperature) were used.

Example 1

Preparation of 2,3-O-isopropylidene-1-O-dodecyl-4-(phenylcarbamate)-6-deoxy-6-hexa-methyleneimino-α-L-xylo-2-hexulofuranose 2,3-O-Isopropylidene-1-O-dodecyl-6-deoxy-6-hexamethyleneimino-α-L-xylo-2-hexulofuranose (prepared according to the method described in U.S. Pat. No. 5,637,570) (2.0 gm) was dissolved in dry methylene chloride (20 ml). To this solution was added phenyl isocyanate (0.64 gm) dropwise at 0–10° C. and the reaction mixture was stirred at the same temperature for 2 hours. It was then washed with water (2 times 5 ml) and brine (2 times 5 ml). The organic layer was dried and the solvent was removed. The crude product so obtained was purified by column chromatography and eluted with 50% ethylacetate in hexane. Pure product yield: 61%.

The following compounds were synthesized similarly by reacting 2,3-O-isopropylidene-1-O-dodecyl-6-deoxy-6-hexamethyleneimino-α-L-xylo-2-hexulofuranose with a suitable isocyanate:

2,3-O-isopropylidene-1-O-dodecyl-4-(p-chlorophenylcarbamate)-6-deoxy-6-hexamethyleneimino-α-L-xylo-2-hexulofuranose 2,3-O-isopropylidene-1-O-dodecyl-4-(p-tolylcarbamate)-6-deoxy-6-hexamethyleneimino-α-L-xylo-2-hexulofuranose 2,3-O-isopropylidene-1-O-dodecyl-4-(p-methoxyphenylcarbamate)-6-deoxy-6-hexamethyleneimino-α-L-xylo-2-hexulofuranose 2,3-O-isopropylidene-1-O-dodecyl-4-(p-nitrophenylcarbamate)-6-deoxy-6-hexamethyleneimino-α-L-xylo-2-hexulofuranose 2,3-O-isopropylidene-1-O-dodecyl-4-(methylcarbamate)-6-deoxy-6-hexamethyleneimino-α-L-xylo-2-hexulofuranose.

Example 2

Preparation of 2,3-O-isopropylidene-1-O-decyl-4-(phenylcarbamate)-6-deoxy-6-pyrrolidinyl-α-L-xylo-2-hexulofuranose 2,3-O-isopropylidene-1-O-dodecyl-6-deoxy-6-pyrrolidinyl-α-L-xylo-2-hexulofuranose (prepared as described in Example 1 by replacing the hexamethyleneimino group with pyrrolidine at position 6) (1.9 gm) was dissolved in methylene chloride (20 ml). To this solution was added phenyl isocyanate (0.56 gm) dropwise at 0–10° C. and the reaction mixture was stirred at the same temperature for 2 hours. The organic layer was washed with water (2 times 10 ml), followed by saturated solution of sodium chloride (2 times 10 ml), dried over anhydrous sodium sulfate and filtered. The solvent was removed with rotary evaporation. The crude product so obtained was purified by flash chromatography using silica gel and eluted with 30% ethylacetate in hexane. Pure product yield: 53.80% (1.0 gm).

The following compounds were synthesized similarly by reacting 2,3-O-isopropylidene-1-O-dodecyl-6-deoxy-6-pyrrolidinyl-α-L-xylo-2-hexulofuranose with a suitable isocyanate:
2,3-O-isopropylidene-1-O-dodecyl-4-(p-chlorophenylcarbamate)-6-deoxy-6-pyrrolidinyl-α-L-xylo-2-hexulofuranose
2,3-O-isopropylidene-1-O-dodecyl-4-(p-tolylcarbamate)-6-deoxy-6-pyrrolidinyl-α-L-xylo-2-hexulofuranose
2,3-O-isopropylidene-1-O-dodecyl-4-(p-methoxyphenylcarbamate)-6-deoxy-6-pyrrolidinyl-α-L-xylo-2-hexulofuranose
2,3-O-isopropylidene-1-O-dodecyl-4-(p-nitrophenylcarbamate)-6-deoxy-6-pyrrolidinyl-α-L-xylo-2-hexulofuranose
2,3-O-isopropylidene-1-O-dodecyl-4-(methylcarbamate)-6-deoxy-6-pyrrolidinyl-α-L-xylo-2-hexulofuranose.

Example 3

Preparation of 2,3-O-isopropylidene-1-O-decyl-4-(phenylcarbamate)-6-deoxy-6-morpholinyl-α-L-xylo-2-hexulofuranose 2,3-O-Isopropylidene-1-O-dodecyl-6-deoxy-6-morpholinyl-α-L-xylo-2-hexulofuranose (prepared as described in Example 1 by replacing the hexamethyleneimino group with the morpholine group at position 6) (2.0 gm) was dissolved in methylene chloride (20 ml). To this solution was added phenyl isocyanate (1.0 ml) dropwise at 0–10° C. and the reaction mixture was stirred at the same temperature for 2 hours. The organic layer was washed with water (2 times 10 ml), followed by saturated solution of sodium chloride (2 times 10 ml), dried over anhydrous sodium sulfate and filtered. The solvent was removed with rotary evaporation. The crude product so obtained was purified by flash chromatography using silica gel and eluted with 30% ethylacetate in hexane. Pure product yield: 54.6% (1.20 gm).

The following compounds were synthesized similarly by reacting 2,3-O-isopropylidene-1-O-dodecyl-6-deoxy-6-morpholinyl-α-L-xylo-2-hexulofuranose with a suitable isocyanate:
2,3-O-isopropylidene-1-O-dodecyl-4-(p-chlorophenylcarbamate)-6-deoxy-6-morpholinyl-α-L-xylo-2-hexulofuranose
2,3-O-isopropylidene-1-O-dodecyl-4-(p-tolylcarbamate)-6-deoxy-6-morpholinyl-α-L-xylo-2-hexulofuranose
2,3-O-isopropylidene-1-O-dodecyl-4-(p-methoxyphenylcarbamate)-6-deoxy-6-morpholinyl-α-L-xylo-2-hexulofuranose
2,3-O-isopropylidene-1-O-dodecyl-4-(p-nitrophenylcarbamate)-6-deoxy-6-morpholinyl-α-L-xylo-2-hexulofuranose
2,3-O-isopropylidene-1-O-dodecyl-4-(methylcarbamate)-6-deoxy-6-morpholinyl-α-L-xylo-2-hexulofuranose.

Example 4

Preparation of 2,3-O-Isopropylidene-1-O-dodecyl-4-(phenylcarbamate)-6-deoxy-6-piperidinyl-α-L-xylo-2-hexulofuranose 2,3-O-Isopropylidene-1-O-dodecyl-6-deoxy-6-morpholinyl-α-L-xylo-2-hexulofuranose (prepared as described in Example 1 by replacing the hexamethyleneimino group with the piperidino group at position 6) (2.0 gm) was dissolved in methylene chloride (20 ml). To this solution was added phenyl isocyanate (0.58 gm) dropwise at 0–10° C. and the reaction mixture was stirred at the same temperature for 2 hours. The reaction was monitored with thin layer chromatography (TLC). The organic layer was washed with water (2 times 10 ml), followed by saturated solution of sodium chloride (2 times 10 ml), dried over anhydrous sodium sulfate and filtered. The solvent was removed with rotary evaporation. The crude product so obtained was purified by flash chromatography using silica gel and eluted with 30% ethylacetate in hexane. Pure product yield: 35.1% (0.90 gm).

The following compounds were synthesized similarly by reacting 2,3-O-isopropylidene-1-O-dodecyl-6-deoxy-6-piperidinyl-α-L-xylo-2-hexulofuranose with a suitable isocyanate:
2,3-O-isopropylidene-1-O-dodecyl-4-(p-chlorophenylcarbamate)-6-deoxy-6-piperidinyl-α-L-xylo-2-hexulofuranose
2,3-O-isopropylidene-1-O-dodecyl-4-(p-tolylcarbamate)-6-deoxy-6-piperidinol-α-L-xylo-2-hexulofuranose
2,3-O-isopropylidene-1-O-dodecyl-4-(p-methoxyphenylcarbamate)-6-deoxy-6-piperidinyl-α-L-xylo-2-hexulofuranose
2,3-O-isopropylidene-1-O-dodecyl-4-(p-nitrophenylcarbamate)-6-deoxy-6-piperidinyl-α-L-xylo-2-hexulofuranose
2,3-O-isopropylidene-1-O-dodecyl-4-(methylcarbamate)-6-deoxy-6-piperidinyl-α-L-xylo-2-hexulofuranose.

Example 5

Preparation of 2,3-O-isopropylidene-1-O-decyl-4-(phenylcarbamate)-6-deoxy-6-(2-ethylpyrrolidinyl)-α-L-xylo-2-hexulofuranose 2,3-O-Isopropylidene-1-O-dodecyl-6-deoxy-6-(2-ethylpyrrolidinyl)-α-L-xylo-2-hexulofuranose (prepared as described in Example 1 by replacing the hexamethyleneimino group with the 2-ethylpyrrolidinyl group at position 6) (1.5 gm) was dissolved in methylene chloride (20 ml). To this solution was added phenyl isocyanate (1.0 ml) dropwise at 0–10° C. and the reaction mixture was stirred at the same temperature for 2 hours. The reaction was monitored with TLC. The organic layer was washed with water (2 times 10 ml), followed by saturated solution of sodium chloride (2 times 10 ml), dried over anhydrous sodium sulfate and filtered. The solvent was removed with rotary evaporation. The crude product so obtained was purified by flash chromatography using silica gel and eluted with 30% ethylacetate in hexane. Pure product yield: 60.2% (1.1 gm).

The following compounds were synthesized similarly by reacting 2,3-O-isopropylidene-1-O-dodecyl-6-deoxy-6-(2-ethylpyrrolidinyl)-α-L-xylo-2-hexulofuranose with a suitable isocyanate:

2,3-O-isopropylidene-1-O-dodecyl-4-(p-chlorophenylcarbamate)-6-deoxy-6-(2-ethylpyrrolidinyl)-α-L-xylo-2-hexulofuranose 2,3-O-isopropylidene-1-O-dodecyl-4-(p-tolylcarbamate)-6-deoxy-6-(2-ethylpyrrolidinyl)-α-L-xylo-2-hexulofuranose 2,3-O-isopropylidene-1-O-dodecyl-4-(p-methoxyphenylcarbamate)-6-deoxy-6-(2-ethylpyrrolidinyl)-α-L-xylo-2-hexulofuranose 2,3-O-isopropylidene-1-O-dodecyl-4-(p-nitrophenylcarbamate)-6-deoxy-6-(2-ethylpyrrolidinyl)-α-L-xylo-2-hexulofuranose 2,3-O-isopropylidene-1-O-dodecyl-4-(methylcarbamate)-6-deoxy-6-(2-ethylpyrroldinyl)-α-L-xylo-2-hexulofuranose.

Example 6

Preparation of 2,3,O-isopropylidene-1-O-dodecyl-4-(phenylcarbamate)-6-deoxy-6-(2-ethylmorpholinyl)-α-L-xylo-2-hexulofuranose 2,3-O-Isopropylidene-1-O-dodecyl-6-deoxy-6-(2-ethylmorpholinyl)-α-L-xylo-2-hexulofuranose (prepared as described in Example 1 by replacing the hexamethyleneimino group with the 2-ethylmorpholino group at position 6) (2.0 gm) was dissolved in methylene chloride (20 ml). To this solution was added phenyl isocyanate (0.56 gm) dropwise at 0–10° C. and the reaction mixture was stirred at the same temperature for 2 hours. The reaction was monitored with TLC. The organic layer was washed with water (2 times 10 ml), followed by saturated solution of sodium chloride (2 times 10 ml), dried over anhydrous sodium sulfate and filtered. The solvent was removed with rotary evaporation. The crude product so obtained was purified by flash chromatography using silica gel and eluted with 30% ethylacetate in hexane. Pure product yield: 30.4% (0.75 gm).

The following compounds were synthesized similarly by reacting 2,3-O-isopropylidene-1-O-dodecyl-6-deoxy-6-(2-ethylmorpholinyl)-α-L-xylo-2-hexulofuranose with a suitable isocyanate:

2,3-O-isopropylidene-1-O-dodecyl-4-(p-chlorophenylcarbamate)-6-deoxy-6-(2-ethylmorpholinyl)-α-L-xylo-2-hexulofuranose 2,3-O-isopropylidene-1-O-dodecyl-4-(p-tolylcarbamate)-6-deoxy-6-(2-ethylmorpholinyl)-α-L-xylo-2-hexulofuranose 2,3-O-isopropylidene-1-O-dodecyl-4-(p-methoxyphenylcarbamate)-6-deoxy-6-(2-ethylmorpholinyl)-α-L-xylo-2-hexulofuranose 2,3-O-isopropylidene-1-O-dodecyl-4-(p-nitrophenylcarbamate)-6-deoxy-6-(2-ethylmorpholinyl)-α-L-xylo-2-hexulofuranose 2,3-O-isopropylidene-1-O-dodecyl-4-(methylcarbamate)-6-deoxy-6-(2-ethylmorpholinyl)-α-L-xylo-2-hexulofuranose.

Example 7

Preparation of 2,3,O,-isopropylid ne-1-O-decyl-4-(phenylcarbamate)-6-deoxy-6-pyrrolidinyl-α-L-xylo-2-hexulofuranose This compound was prepared according to method described in Example 2 by reacting 2,3-O-isopropylidene-1-O-decyl-6-deoxy-6-pyrrolidinyl-α-L-xylo-2-hexulofuranose with phenyl isocyanate at 0–10° C. Pure product yield: 58%.

The following compounds were synthesized similarly by reacting 2,3-O-isopropylidene-1-O-decyl-6-deoxy-6-pyrrolidinyl-α-L-xylo-2-hexulofuranose with the desired isocyanate:

2,3-O-isopropylidene-1-O-dodecyl-4-(p-chlorophenylcarbamate)-6-deoxy-6-pyrrolidinyl-α-L-xylo-2-hexulofuranose 2,3-O-isopropylidene-1-O-dodecyl-4-(p-tolylcarbamate)-6-deoxy-6-pyrrolidinyl-α-L-xylo-2-hexulofuranose 2,3-O-isopropylidene-1-O-dodecyl-4-(p-methoxyphenylcarbamate)-6-deoxy-6-pyrrolidinyl-α-L-xylo-2-hexulofuranose 2,3-O-isopropylidene-1-O-dodecyl-4-(p-nitrophenylcarbamate)-6-deoxy-6-pyrrolidinyl-α-L-xylo-2-hexulofuranose 2,3-O-isopropylidene-1-O-dodecyl-4-(methylcarbamate)-6-deoxy-6-pyrrolidinyl-α-L-xylo-2-hexulofuranose.

Example 8

Preparation of 2,3,0-isopropylidene-1-O-decyl-4-(phenylcarbamate)-6-deoxy-6-morpholinyl-α-L-xylo-2-hexulofuranose This compound was prepared according to the method described in Example 3 by reacting 2,3-O-isopropylidene-1-O-decyl-6-deoxy-6-morpholinyl-α-L-xylo- 2-hexulofuranose with phenyl isocyanate at 0–10° C. Pure product yield: 61%.

The following compounds were synthesized similarly by reacting 2,3-O-isopropylidene-1-O-decyl-6-deoxy-6-morpholinyl-α-L-xylo-2-hexulofuranose with the desired isocyanate:

2,3-O-isopropylidene-1-O-decyl-4-(p-chlorophenylcarbamate)-6-deoxy-6-morpholinyl-α-L-xylo-2-hexulofuranose 2,3-O-isopropylidene-1-O-decyl-4-(p-tolylcarbamate)-6-deoxy-6-morpholinyl-α-L-xylo-2-hexulofuranose 2,3-O-isopropylidene-1-O-decyl-4-(p-methoxyphenylcarbamate)-6-deoxy-6-morpholinyl-α-L-xylo-2-hexulofuranose 2,3-O-isopropylidene-1-O-decyl-4-(p-nitrophenylcarbamate)-6-deoxy-6-morpholinyl-α-L-xylo-2-hexulofuranose 2,3-O-isopropylidene-1-O-decyl-4-(methylcarbamate)-6-deoxy-6-morpholinyl-α-L-xylo-2-hexulofuranose.

Example 9

Preparation of 2,3-O-isopropylidene-1-O-decyl-4-(phenylcarbamate)-6-deoxy-6-hexamethyleneimino-α-L-xylo-2-hexulofuranose This compound was prepared according to the method described in Example 1 by reacting 2,3-O-isopropylidene-1-O-decyl-6-deoxy-6 examethyleneimino-α-L-xylo-2-hexulofuranose with phenyl isocyanate at 0–10° C. Pure product yield: 69%.

The following compounds were synthesized similarly by reacting 2,3-O-isopropylidene-1-O-decyl-6-deoxy-6-hexamethyleneimino-α-L-xylo-2-hexulofuranose with the desired isocyanate:

2,3-O-isopropylidene-1-O-decyl-4-(p-chlorophenylcarbamate)-6-deoxy-6-hexamethyleneimino-α-L-xylo-2-hexulofuranose 2,3-O-isopropylidene-1-O-decyl-4-(p-tolylcarbamate)-6-deoxy-6-hexamethyleneimino-α-L-xylo-2-hexulofuranose 2,3-O-isopropylidene-1-O-decyl-4-(p-methoxyphenylcarbamate)-6-deoxy-6-hexamethyleneimino-α-L-xylo-2-hexulofuranose 2,3-O-isopropylidene-1-O-decyl-4-(p-nitrophenylcarbamate)-6-deoxy-6-hexamethyleneimino-α-L-xylo-2-hexulofuranose 2,3-O-isopropylidene-1-O-decyl-4-(methylcarbamate)-6-deoxy-6-hexamethyleneimino-α-L-xylo-2-hexulofuranose.

Example 10

Preparation of 2,3-O-isopropylidene-1-O-decyl-4-(phenylcarbamate)-6-deoxy-6-piperidinyl-α-L-xylo-2-hexulofuranose This compound was prepared-according to the method described in Example 3 by reacting 2,3-O-isopropylidene-1-O-decyl-6-deoxy-6-piperidinyl-α-L-xylo-2-hexulofuranose with phenyl isocyanate at 0–10° C. Pure product yield: 74%.

The following compounds were synthesized similarly by reacting 2,3-O-isopropylidene-1-O-decyl-6-deoxy-6-piperidinyl-α-L-xylo-2-hexulofuranose with the desired isocyanate:

2,3-O-isopropylidene-1-O-decyl-4-(p-chlorophenylcarbamate)-6-deoxy-6-piperidinyl-α-L-xylo-2-hexulofuranose 2,3-O-isopropylidene-1-O-decyl-4-(p-tolylcarbamate)-6-deoxy-6-piperidinyl-α-L-xylo-2-hexulofuranose 2,3-O-isopropylidene-1-O-decyl-4-(p-methoxyphenylcarbamate)-6-deoxy-6-piperidinyl-α-L-xylo-2-hexulofuranose 2,3-O-isopropylidene-1-O-decyl-4-(p-nitrophenylcarbamate)-6-deoxy-6-piperidinyl-α-L-xylo-2-hexulofuranose 2,3-O-isopropylidene-1-O-decyl-4-(methylcarbamate)-6-deoxy-6-piperidinyl-α-L-xylo-2-hexulofuranose.

Example 11

Preparation of 2,3-O-isopropylidene-1-O-decyl-4-(phenylcarbamate)-6-deoxy-6-(2-ethylpyrrolidinyl)-α-L-xylo-2-hexulofuranose This compound was prepared according to the method described in Example 3 by reacting 2,3-O-isopro-pylidene-1-O-decyl-6-deoxy-6-(2-ethylpyrrolidinyl)-α-L-xylo-2-hexulofuranose with phenyl isocyanate at 0–10° C. Pure product yield: 74%.

The following compounds were synthesized similarly by reacting 2,3-O-isopropylidene-1-O-decyl-6-deoxy-6-(2-ethylpyrrolidinyl)-α-L-xylo-2-hexulofuranose with the desired isocyanate:

2,3-O-isopropylidene-1-O-decyl-4-(p-chlorophenylcarbamate)-6-deoxy-6-(2-ethylpyrrolidinyl)-α-L-xylo-2-hexulofuranose 2,3-O-isopropylidene-1-O-decyl-4-(p-tolylcarbamate)-6-deoxy-6-7(2-ethylpyrrolidinyl)-α-L-xylo-2-hexulofuranose 2,3-O-isopropylidene-1-O-decyl-4-(p-methoxyphenylcarbamate)-6-deoxy-6-(2-ethylpyrrolidinyl)-α-L-xylo-2-hexulofuranose 2,3-O-isopropylidene-1-O-decyl-4-(p-nitrophenylcarbamate)-6-deoxy-6-(2-ethylpyrrolidinyl)-α-L-xylo-2-hexulofuranose 2,3-O-isopropylidene-1-O-decyl-4-(methylcarbamate)-6-deoxy-6-(2-ethylpyrrolidinyl)-α-L-xylo-2-hexulofuranose.

Example 12

Preparation of 2,3-O-isopropylidene-1-O-decyl-4-(phenylcarbamate)-6-deoxy-6-(2-ethylmorpholinyl)-α-L-xylo-2-hexulofuranose This compound was prepared according to the method described in Example 3 by reacting 2,3-O-isopropylidene-1-O-decyl-6-deoxy-6-(2-ethylmorpholinyl)-α-L-xylo-2-hexulofuranose with phenyl isocyanate at 0–10°C. Pure product yield: 72%.

The following compounds were synthesized similarly by reacting 2,3-O-isopropylidene-1-O-decyl-6-deoxy-6-(2-ethylmorpholinyl)-α-L-xylo-2-hexulofuranose with the desired isocyanate:

2,3-O-isopropylidene-1-O-decyl-4-(p-chlorophenylcarbamate)-6-deoxy-6-(2-ethylmorpholinyl)-α-L-xylo-2-hexulofuranose 2,3-O-isopropylidene-1-O-decyl-4-(p-tolylcarbamate)-6-deoxy-6-(2-ethylmorpholinyl)-α-L-xylo-2-hexulofuranose 2,3-O-isopropylidene-1-O-decyl-4-(p-methoxyphenylcarbamate)-6-deoxy-6-(2-ethylmorpholinyl)-α-L-xylo-2-hexulofuranose 2,3-O-isopropylidene-1-O-decyl-4-(p-nitrophenylcarbamate)-6-deoxy-6-(2-ethylmorpholinyl)-α-L-xylo-2-hexulofuranose 2,3-O-isopropylidene-1-O-decyl-4-(methylcarbamate)-6-deoxy-6-(2-ethylmorpholinyl)-α-L-xylo-2-hexulofuranose.

Example 13

Preparation of 2,3-O-isopropylidene-1-O-heptyl-4-(phenylcarbamate)-6-deoxy-6-pyrrolidinyl-α-L-xylo-2-hexulofuranose This compound was prepared according to the method described in Example 2 by reacting 2,3-O-isopropylidene-1-O-heptyl-6-deoxy-6-pyrrolidinyl-α-L-xylo-2-hexulofuranose with phenyl isocyanate at 0–10° C. Pure product yield: 85.4%

The following compounds were synthesized similarly by reacting 2,3-O-isopropylidene-1-O-heptyl-6-deoxy-6-pyrrolidinyl-α-L-xylo-2-hexulofuranose with the desired isocyanate:

2,3-O-isopropylidene-1-O-heptyl-4-(p-chlorophenylcarbamate)-6-deoxy-6-pyrrolidinyl-α-L-xylo-2-hexulofuranose 2,3-O-isopropylidene-1-O-heptyl-4-(p-tolylcarbamate)-6-deoxy-6-pyrrolidinyl-α-L-xylo-2-hexulofuranose 2,3-O-isopropylidene-1-O-heptyl-4-(p-methoxyphenylcarbamate)-6-deoxy-6-pyrrolidinyl-α-L-xylo-2-hexulofuranose 2,3-O-isopropylidene-1-O-heptyl-4-(p-nitrophenylcarbamate)-6-deoxy-6-pyrrolidinyl-α-L-xylo-2-hexulofuranose 2,3-O-isopropylidene-1-O-heptyl-4-(methylcarbamate)-6-deoxy-6-pyrrolidinyl-α-L-xylo-2-hexulofuranose.

Example 14

Preparation of 2,3-O-isopropylidene-1-O-heptyl-4-(phenylcarbamate)-6-deoxy-6-morpholinyl-α-L-xylo-2-hexulofuranose This compound was prepared according to the method described in Example 3 by reacting 2,3-O-isopropylidene-1-O-heptyl-6-deoxy-6-morpholinyl-α-L-xylo-2-hexulofuranose with phenyl isocyanate at 0–10° C. Pure product yield: 79%.

The following compounds were synthesized similarly by reacting 2,3-O-isopropylidene-1-O-decyl-6-deoxy-6-morpholinyl-α-L-xylo-2-hexulofuranose with the desired isocyanate:

2,3-O-isopropylidene-1-O-heptyl-4-(p-chlorophenylcarbamate)-6-deoxy-6-morpholinyl-α-L-xylo-2-hexulofuranose 2,3-O-isopropylidene-1-O-heptyl-4-(p-tolylcarbamate)-6-deoxy-6-morpholinyl-α-L-xylo-2-hexulofuranose 2,3-O-isopropylidene-1-O-heptyl-4-(p-methoxyphenylcarbamate)-6-deoxy-6-morpholinyl-α-L-xylo-2-hexulofuranose 2,3-O-isopropylidene-1-O-heptyl-4-(p-nitrophenylcarbamate)-6-deoxy-6-morpholinyl-α-L-xylo-2-hexulofuranose 2,3-O-isopropylidene-1-O-heptyl-4-(methylcarbamate)-6-deoxy-6-morpholinyl-α-L-xylo-2-hexulofuranose.

Example 15

Preparation of 2,3-O-Isopropylidene-1-O-heptyl-4-(phenylcarbamate)-6-deoxy-6-hexamethyleneimino-α-L-xylo-2-hexulofuranose This compound was prepared according to the method described in Example 3 by reacting 2,3-O-isopropylidene-1-O-heptyl-6-deoxy-6-hexamethylene-imino-α-L-xylo-2-hexulofuranose with phenyl isocyanate at 0–10° C. Pure product yield: 91%.

The following compounds were synthesized similarly by reacting 2,3-O-isopropylidene-1-O-heptyl-6-deoxy-6-hexamethyleneimino-α-L-xylo-2-hexulofuranose with the desired isocyanate:

2,3-O-isopropylidene-1-O-heptyl-4-(p-chlorophenylcarbamate)-6-deoxy-6-hexamethyleneimino-α-L-xylo-2-hexulofuranose 2,3-O-isopropylidene-1-O-heptyl-4-(p-tolylcarbamate)-6-deoxy-6-hexamethyleneimino-α-L-xylo-2-hexulofuranose 2,3-O-isopropylidene-1-O-heptyl-4-(p-methoxyphenylcarbamate)-6-deoxy-6-hexamethyleneimino-α-L-xylo-2-hexulofuranose 2,3-O-isopropylidene-1-O-heptyl-4-(p-nitrophenylcarbamate)-6-deoxy-6-hexamethyleneimino-α-L-xylo-2-hexulofuranose 2,3-O-isopropylidene-1-O-heptyl-4-(methylcarbamate)-6-deoxy-6-hexamethyleneimino-α-L-xylo-2-hexulofuranose.

Example 16

Preparation of 2,3-O-isopropylidene-1-O-heptyl-4-(phenylcarbamat )-6-deoxy-6-piperidinyl-α-L-xylo-2-hexulofuranose This compound was prepared according to the method described in Example 3 by reacting 2,3-O-isopropylidene-1-O-heptyl-6-deoxy-6-piperidinyl-α-L-xylo-2-hexulofuranose with phenyl isocyanate at 0–10° C. Pure product yield: 47.6%.

The following compounds were synthesized similarly by-reacting 2,3-O-isopropylidene-1-O-heptyl-6-deoxy-6-piperidinyl-α-L-xylo-2-hexulofuranose with the desired isocyanate:

2,3-O-isopropylidene-1-O-heptyl-4-(p-chlorophenylcarbamate)-6-deoxy-6-piperidinyl-α-L-xylo-2-hexulofuranose 2,3-O-isopropylidene-1-O-heptyl-4-(p-tolylcarbamate)-6-deoxy-6-piperidinyl-α-L-xylo-2-hexulofuranose 2,3-O-isopropylidene-1-O-heptyl-4-(p-methoxyphenylcarbamate)-6-deoxy-6-piperidinyl-α-L-xylo-2-hexulofuranose 2,3-O-isopropylidene-1-O-heptyl-4-(p-nitrophenylcarbamate)-6-deoxy-6-piperidinyl-α-L-xylo-2-hexulofuranose 2,3-O-isopropylidene-1-O-heptyl-4-(methylcarbamate)-6-deoxy-6-piperidinyl-α-L-xylo-2-hexulofuranose.

Example 17

Preparation of 2,3-O-isopropylidene-1-O-heptyl-4-(phenylcarbamate)-6-deoxy-6-(2-ethylpyrrolidinyl)-α-L-xylo-2-hexulofuranose This compound was prepared according to the method described in Example 3 by reacting 2,3-O-isopropylidene-1-O-heptyl-6-deoxy-6-(2-ethylpyrrolidinyl)-α-L-xylo-2-hexulofuranose with phenyl isocyanate at 0–10° C. Pure product yield: 68%.

The following compounds were synthesized similarly by reacting 2,3-O-isopropylidene-1-O-heptyl-6-deoxy-6-(2-ethylpyrrolidinyl)-α-L-xylo-2-hexulofuranose with the desired isocyanate:

2,3-O-isopropylidene-1-O-heptyl-4-(p-chlorophenylcarbamate)-6-deoxy-6-(2-ethylpyrrolidinyl)-α-L-xylo-2-hexulofuranose 2,3-O-isopropylidene-1-O-heptyl-4-(p-tolylcarbamate)-6-deoxy-6-(2-ethylpyrrolidinyl)-α-L-xylo-2-hexulofuranose 2,3-O-isopropylidene-1-O-heptyl-4-(p-methoxyphenylcarbamate)-6-deoxy-6-(2-ethylpyrrolidinyl)-α-L-xylo-2-hexulofuranose 2,3-O-isopropylidene-1-O-heptyl-4-(p-nitrophenylcarbamate)-6-deoxy-6-(2-ethylpyrrolidinyl)-α-L-xylo-2-hexulofuranose 2,3-O-isopropylidene-1-O-heptyl-4-(methylcarbamate)-6-deoxy-6-(2-ethylpyrrolidinyl)-α-L-xylo-2-hexulofuranose.

Example 18

Preparation of 2,3-O-isopropylidene-1-O-heptyl-4-(phenylcarbamate)-6-deoxy-6-(2-ethylmorpholinyl)-α-L-xylo-2-hexulofuranose This compound was prepared similarly according to the method described in Example 3 by reacting 2,3-O-isopropylidene-1-O-heptyl-6-deoxy-6-(2-ethylmorpholinyl)-α-L-xylo-2-hexulofuranose with phenyl isocyanate at 0–10° C. Pure product yield: 75.8%.

The following compounds were synthesized similarly by reacting the 2,3-O-isopropylidene-1-O-heptyl-6-deoxy-6-(2-ethylmorpholinyl)-α-L-xylo-2-hexulofuranose with the desired isocyanate:

2,3-O-isopropylidene-1-O-heptyl-4-(p-chlorophenylcarbamate)-6-deoxy-6-(2-ethylmorpholinyl)-α-L-xylo-2-hexulofuranose 2,3-O-isopropylidene-1-O-heptyl-4-(p-tolylcarbamate)-6-deoxy-6-(2-ethylmorpholinyl)-α-L-xylo-2-hexulofuranose 2,3-O-isopropylidene-1-O-heptyl-4-(p-methoxyphenylcarbamate)-6-deoxy-6-(2-ethylmorpholinyl)-α-L-xylo-2-hexulofuranose 2,3-O-isopropylidene-1-O-heptyl-4-(p-nitrophenylcarbamate)-6-deoxy-6-(2-ethylmorpholinyl)-α-L-xylo-2-hexulofuranose 2,3-O-isopropylidene-1-O-heptyl-4-(methylcarbamate)-6-deoxy-6-(2-ethylmorpholinyl)-α-L-xylo-2-hexulofuranose.

While the present invention has been described in terms of its specific embodiments, certain modifications and equivalents will be apparent to those skilled in the art and are intended to be included within the scope of this invention, which is to be limited only by the scope of the appended claims.

What is claimed is:

1. The method of inhibiting or suppressing cell adhesion in an animal comprising administering to said animal, a compound having the structure of Formula I:

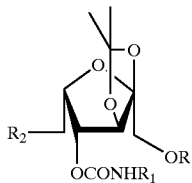

FORMULA I or its pharmaceutically acceptable salts, esters, enantiomers, diastereomers, N oxides, amides, wherein R is $C_1$ to $C_{15}$ alkyl, alkene, alkyne (straight chain or branched), aryl, or alkylaryl and $R_1$ is methyl, phenyl, o,-m- or p-chlorophenyl, tolyl, methoxyphenyl or nitrophenyl and $R_2$ is H, pyrrolidinyl, piperidinyl, morphilinyl or hexamethyleneimino or a radical of the formula $NHR_3$, wherein $R_3$ is $C_1$ to $C_{15}$ alkyl, alkene or alkyne (straight chain or branched) or a radical of Formula III:

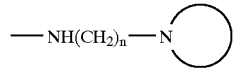

FORMULA III in which n is 2 to 5 and

is a five-, six- or seven-membered heterocyclic ring containing one or more heteroatoms.

2. The method of claim 1, wherein

is pyrrolidinyl, piperidinyl, morpholinyl or hexamethyleneimino moieties.

3. The method according to claim 1 wherein the cell adhesion is associated with inflammation.

4. The method according to claim 1 wherein the cell adhesion is associated with immune or autoimmune response.

5. A method of inhibiting or suppressing cell adhesion in an animal comprising the step of administering to said animal a pharmaceutical composition comprising a pharmaceutically effective amount of a compound having the structure of Formula I

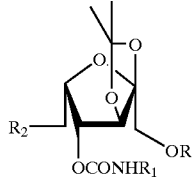

FORMULA I or its pharmaceutically acceptable salts, esters, enantiomers, diastereomers, N-oxides, amides, wherein R is $C_1$ to $C_{15}$ alkyl, alkene, alkyne (straight chain or branched), aryl, or alkylaryl and $R_1$ is methyl, phenyl o-, m- or p-chlorophenyl, tolyl, methoxyphenyl or nitrophenyl and $R_2$ is H, pyrrolidinyl, piperidinyl, morpholinyl or hexamethyleneimino or a radical of the formula $NHR_3$, wherein $R_3$ is $C_1$ to $C_{15}$ alkyl, alkene or alkyne (straight chain or branched) or a radical of Formula III:

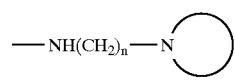

FORMULA III wherein n is 2 to 5 and

is a five-, six- or seven-membered heterocyclic ring containing one or more heteroatoms and a pharmaceutically acceptable carrier.

* * * * *